US011000552B2

(12) United States Patent
Yoshimura et al.

(10) Patent No.: US 11,000,552 B2
(45) Date of Patent: May 11, 2021

(54) PLURIPOTENT STEM CELL FOR TREATING DIABETIC SKIN ULCER

(71) Applicants: The University of Tokyo, Tokyo (JP); Tohoku University, Miyagi (JP)

(72) Inventors: Kotaro Yoshimura, Tokyo (JP); Kahori Kinoshita, Tokyo (JP); Mari Dezawa, Miyagi (JP)

(73) Assignees: The University of Tokyo, Tokyo (JP); Tohoku University, Miyagi (JP)

( * ) Notice: Subject to any disclaimer, the term of this patent is extended or adjusted under 35 U.S.C. 154(b) by 0 days.

(21) Appl. No.: 16/288,705

(22) Filed: Feb. 28, 2019

(65) Prior Publication Data

US 2019/0192574 A1    Jun. 27, 2019

Related U.S. Application Data

(62) Division of application No. 15/508,872, filed as application No. PCT/JP2015/067789 on Jun. 19, 2015, now abandoned.

(30) Foreign Application Priority Data

Sep. 5, 2014  (JP) .................. 2014-181463

(51) Int. Cl.
*A61K 35/28*    (2015.01)
*A61K 35/12*    (2015.01)
(Continued)

(52) U.S. Cl.
CPC .............. *A61K 35/28* (2013.01); *A61K 35/12* (2013.01); *A61K 35/545* (2013.01); *A61P 3/10* (2018.01); *A61P 17/02* (2018.01)

(58) Field of Classification Search
None
See application file for complete search history.

(56) References Cited

U.S. PATENT DOCUMENTS 9,694,035 B2    7/2017  Aggarwal et al.
9,943,547 B2    4/2018  Aggarwal et al.
(Continued)

FOREIGN PATENT DOCUMENTS

CN    103442724 A    12/2013
JP      4183742 B    11/2008
(Continued)

OTHER PUBLICATIONS

PCT/JP2015/067789—International Search Report dated Aug. 11, 2015, 5 pages (with English Translation).
(Continued)

*Primary Examiner* — Erin M. Bowers
(74) *Attorney, Agent, or Firm* — Mintz Levin Cohn Ferris Glovsky and Popeo PC

(57) ABSTRACT

The purpose of the present invention is to provide a novel medicinal use in regeneration medicine, said medicinal use comprising using pluripotent stem cells (Muse cells). Provided is a cell preparation for treating skin ulcer, said cell preparation comprising SSEA-3 positive pluripotent stem cells isolated from a mesenchymal tissue of a living organism or cultured mesenchymal cells. The cell preparation according to the present invention is based on such mechanism of skin tissue regeneration that, when the Muse cells are administered to a skin ulcer site of a subject suffering from the aforesaid disease, the Muse cells differentiate into skin-constituting cells.

5 Claims, 5 Drawing Sheets

(51) Int. Cl.
     *A61K 35/545*   (2015.01)
     *A61P 17/02*    (2006.01)
     *A61P 3/10*     (2006.01)

(56) References Cited

U.S. PATENT DOCUMENTS

| | | | |
|---|---|---|---|
| 2008/0193424 A1* | 8/2008 | McKale | A61P 17/02 424/93.7 |
| 2009/0068742 A1 | 3/2009 | Yamanaka | |
| 2010/0111897 A1 | 5/2010 | Katz et al. | |
| 2011/0070647 A1* | 3/2011 | Dezawa | A61P 15/00 435/378 |
| 2011/0104803 A1 | 5/2011 | Tamai et al. | |
| 2012/0244129 A1 | 9/2012 | Dezawa et al. | |
| 2015/0196600 A1 | 7/2015 | Yoshida et al. | |
| 2017/0258844 A1 | 9/2017 | Yoshimura et al. | |

FOREIGN PATENT DOCUMENTS

| | | |
|---|---|---|
| JP | 2010505849 A | 2/2010 |
| JP | 2014-139214 A | 7/2014 |
| WO | 2009133943 A1 | 11/2009 |
| WO | 2011007900 A1 | 1/2011 |
| WO | 2013082543 A1 | 6/2013 |
| WO | 2013/131192 A1 | 9/2013 |
| WO | 2014/027684 A1 | 2/2014 |
| WO | 2014/133090 A1 | 9/2014 |

OTHER PUBLICATIONS

Aoi, N. et al. (2011). "Aratana Master Kansaibo (Muse Saibo) no Riyo ni Mukete," Dai 20 Kai Japan Society of Plastic and Reconstructive Surgery Kiso Gakujutsu Shukai Program Shorokishu, p. 95 with English language translation.

Dezawa, Mari et al., "Specific induction of neuronal cells from bone marrow stromal cells and application for autologous transplantation," *The Journal of Clinical Investigation* (Jun. 2004; accepted in revised form Apr. 20, 2004); 113(12):1701-1710.

Dezawa, Mari et al., "Bone Marrow Stormal Cells Generate Muscle Cells and Repair Muscle Degeneration," *Science* (Jul. 7, 2005); 309:5732:314-317.

Dezawa, M. et al. (2011). "Seitai Yurai no Kan'yokei Soshiki ni Naiho sareru Muse Saibo no Hakken," Experimental Medicine 29(19):3077-3084 with English language translation—Abstract, only.

Dezawa, M., "Saisei Iryo Kenkyu no Genjo to Muse Saibo no Shorai Tenbo," Heisei 26 Nendo Sentan Gijutsu Kenshu Slide, Jun. 20, 2014 (Jun. 20, 2014), 32 pages.

Gang, Eun J. et al., "SSEA-4 identifies mesenchymal stem cells from bone marrow," *Blood* (Feb. 15, 2007); 109(4):1743-1751.

Kim, M.D., Ph.D., Eun Key et al., "The Effect of Human Adipose-Derived Stem Cells on Healing of Ischemic Wounds in a Diabetic Nude Mouse Model," *Plastic and Reconstructive Surgery* (Aug. 2011; accepted Feb. 18, 2011); 128(2):387-394.

Kuroda, Y. et al. (May 11, 2010, e-published Apr. 26, 2010). "Unique multipotent cells in adult human mesenchymal cell populations," Proc Natl Acad Sci USA 107(19):8639-8643.

Kuroda, Yasumasa et al., "Isolation, culture and evaluation of multilineage-differentiating stress-enduring (Muse) Cells," *Nature Protocols* (Jun. 20, 2013); 8(7):1391-1415.

Kuroda, Yasumasa et al., "Mesenchymal Stem Cells and Their Subpopulation, Pluripotent Muse Cells, in Basic Research and Regenerative Medicine," *The Anatomical Record* (2014; published online Dec. 2, 2013); 297:98-110.

Li, Shaoyi et al., "Bystander effect-mediated gene therapy of gliomas using genetically engineered neural stem cells," *Cancer Gene Therapy* (Mar. 18, 2005); 12:600-607.

Marino, M.D., Gerardo et al., "Therapy with autologous adipose-derived regenerative cells for the care of chronic ulcer of lower limbs in patients with peripheral arterial disease," *Journal of Surgical Research* (May 28, 2013) 185:36-44.

Miranville, A. et al. "Improvement of Postnatal Neovascularization by Human Adipose Tissue-Derived Stem Cells," *Circulation* (Jul. 6, 2004) 110:349-355.

Planat-Benard, Ph.D., Valerie et al., "Plasticity of Human Adipose Lineage Cells Toward Endothelial Cells," *Circulation* (Jan. 20, 2004); 109:656-663.

Rehman, M.D., Jalees et al., "Secretion of Angiogenic and Antiapoptotic Factors by Human Adipose Stromal Cells," *Circulation* (Mar. 1, 2004); 109:1292-1298.

Stumvoll, Michael et al., "Type 2 diabetes: principles of pathogenesis and therapy," *Lancet* (Apr. 9, 2005); 365:1333-1346.

Wakao, Shoheii et al., "Multilineage-differentiating stress-enduring (Muse) cells are a primary source of induced pluripotent stem cells in human fibroblasts," *PNAS* (Jun. 14, 2011); 108(24):9875-9880.

Wakao, Shohei et al., "Regenerative Effects of Mesenchymal Stem Cells: Contribution of Muse Cells, a Novel Pluripotent Stem Cell Type that Resides in Mesenchymal Cells," *Cells* (Nov. 8, 2012); 1:1045-1060.

Wakao, Shohei et al., "Muse cells, newly found non-tumorigenic pluripotent stem cells, reside in human mesenchymal tissues," *Pathology International* (2014; accepted for publication Dec. 13, 2013); 64:1-9.

Wu, Yaojiong et al., "Mesenchymal Stem Cells Enhance Wound Healing Through Differentiation and Angiogenesis," *Stem Cells* (Jul. 5, 2007); 25:2648-2659.

* cited by examiner

PLURIPOTENT STEM CELL FOR TREATING DIABETIC SKIN ULCER

TECHNICAL FIELD

The present invention relates to a cell preparation for use in regenerative medicine. More particularly, the present invention relates to a cell preparation comprising pluripotent stem cells effective for repair and regeneration of skin tissue in skin ulcers including skin ulcers caused by diabetes, and to a method for treating skin ulcers that uses these pluripotent stem cells.

BACKGROUND ART

Diabetes is a disease that is associated with persistent hyperglycemic state and is said to occur as a result of the actions of a diverse range of environmental and genetic factors. The main regulatory factor of blood sugar is insulin, and hyperglycemia is known to occur due to insulin deficiency or an excess of factors that inhibit the action thereof (such as genetic predisposition, lack of exercise, obesity or stress). Diabetes is classified as type 1 diabetes, which occurs primarily due to a decrease in pancreatic insulin secretory function attributable to such factors as autoimmune diseases, and type 2 diabetes, which is caused by a decrease in pancreatic insulin secretory function or insulin resistance caused by pancreatic exhaustion associated with persistently high levels of insulin secretion. In Japan, diabetes has become a modern-day national affliction and more than 95% of diabetes patients (which is estimated to exceed 20 million people when including persons at risk to the onset of diabetes) have been diagnosed with non-insulin-dependent diabetes mellitus, and increases in the number of patients is becoming a problem accompanying lifestyle changes. The number of sufferers of diabetes around the world has been estimated at roughly 200 million persons (Non-Patent Document 1), and the global market for antidiabetic drugs is on the order of roughly 1 trillion yen. This makes diabetes the top-ranked disease both in terms of market size and population.

Many serious complications of diabetes such as heart disease, kidney failure or blindness have an effect on individuals together with diabetes, and complications involving the lower extremities result in the greatest damage. As much as 40% to 70% of all lower extremity amputations are related to diabetes mellitus, and in actuality, 85% of all diabetes-related lower extremity amputations occur following ulcers of the leg or foot. Patients afflicted with diabetes mellitus are at greater risk to the onset of chronic skin ulcers such as ulcers of the leg and foot accompanying long-term complications. Ulcers occur as a result of ischemia and/or nerve disorders. Local tissue ischemia is the major cause of diabetic ulcers. Similar to large vessel disease, patients with diabetes are at greater risk to skin perfusion associated with non-conductive arteries during the course of impairment of the microcirculation control mechanism referred to as atherosclerosis or microvascular disease. Under normal circumstances, blood flow increases in order to promote healing in response to injury. However, in cases in which microvascular disease (or ischemia) is present, this response is significantly impaired, and this is considered to most likely be important in the etiology of ulcers together with a tendency towards the occurrence of thrombosis in the microcirculation during reduced blood flow. On the other hand, nerve disorders lack an adequately established treatment method with respect to both the symptomatic treatment thereof and the prevention of the progressive decline of nerve function, and is one of the major complications of diabetes mellitus. The effects of peripheral nerve disorders are particularly complex. Although the mechanism leading to nerve damage associated with diabetes has yet to be fully understood, it is said to involve multiple factors, such as genetic predisposition, metabolic and vascular abnormalities or a lack of perturbation of related growth factors.

Attention is being focused on regenerative medicine using pluripotent stem cells for treatment of the aforementioned refractory diseases. Adipose tissue-derived stromal cells (ASC) are known to be one type of such cells, and are thought to have the ability to differentiate into not only adipocytes and blood vessels, but also various other tissue cells and tissue lines (Non-Patent Documents 2 to 4). An attempt to treat ischemic injury by producing diabetic mice has been reported as an example of the use of ASC (Non-Patent Document 5). In addition, an example of applying adipose-derived regenerative cells to the clinical treatment of diabetic ulcers of the lower extremities of patients afflicted with peripheral arterial diseases has also been reported (Non-Patent Document 6). However, these attempts have not led to complete recovery at the injured site.

In addition, although mesenchymal stem cells (MSC) having the ability to differentiate into bone, cartilage, adipocytes, nerve cells or skeletal muscle and the like are known to be examples of cells obtained from the adult body that have the ability to differentiate (Non-Patent Documents 7 and 8), these constitute a cell population that includes various cells, the actual state of that differentiation ability is not fully understood, and there have been considerable variations in the therapeutic effects thereof. In addition, although iPS cells have been reported to be adult-derived pluripotent stem cells (as reported in Patent Document 1, for example), in addition to the establishment of iPS cells requiring an extremely complex procedure consisting of introducing a specific gene into mesenchymal cells in the form of skin fibroblasts or introducing a specific compound into somatic cells, iPS cells are also highly tumorigenic, thereby resulting in the presence of extremely difficult obstacles to their clinical application.

According to research conducted by Dezawa, one of the inventors of the present invention, pluripotent stem cells present in a mesenchymal cell fraction that express a surface antigen in the form of stage-specific embryonic antigen-3 (SSEA-3) (referred to as multilineage-differentiating stress enduring cells (Muse cells)) are responsible for the pluripotency of that mesenchymal cell fraction, and were determined to have the potential to be applied to disease treatment targeted at tissue regeneration (Patent Document 2, Non-Patent Documents 9 to 12). However, there have yet to be any examples describing the use of Muse cells for the prevention and/or treatment of skin ulcer that clearly demonstrate the obtaining of anticipated therapeutic effects.

PRIOR ART DOCUMENTS

Patent Documents

Patent Document 1: Japanese Patent No. 4183742
Patent Document 2: International Publication No. WO 2011/007900

Non-Patent Documents

Non-Patent Document 1: Stumvoll, M., et al., Lancet, Vol. 365, p. 1333-1346 (2005)

Non-Patent Document 2: Rehman, J., et al., Circulation, Vol. 109, p. 1292-1298 (2004)
Non-Patent Document 3: Planat-Benard, V., et al., Circulation, Vol. 109, p. 656-663 (2004)
Non-Patent Document 4: Miranvile, A., et al., Circulation, Vol. 110, p. 349-355 (2004)
Non-Patent Document 5: Kim, E. K., et al., Plast. Reconstr. Surg., Vol. 128, p. 387-394 (2011)
Non-Patent Document 6: Marino, G., et al., J. Surg. Res., Vol. 185, p. 36-44 (2013)
Non-Patent Document 7: Dezawa, M., et al., J. Clin. Invest., Vol. 113, p. 1701-1710 (2004)
Non-Patent Document 8: Dezawa, M., et al., Science, Vol. 309, p. 314-317 (2005)
Non-Patent Document 9: Li, S., et al., Cancer Gene Therapy, Vol. 12, p. 600-607 (2005)
Non-Patent Document 10: Kuroda, Y., et al., Proc. Natl. Acad. Sci. USA, Vol. 107, p. 8639-8643 (2010)
Non-Patent Document 11: Wakao, S., et al., Proc. Natl. Acad. Sci. USA, Vol. 108, p. 9875-9880 (2011)
Non-Patent Document 12: Kuroda, Y., et al., Nat. Protoco., Vol. 8, p. 1391-1415 (2013)

DISCLOSURE OF THE INVENTION

Problems to be Solved by the Invention

An object of the present invention is to provide a novel medical application using pluripotent stem cells (Muse cells). More specifically, an object of the present invention is to provide a cell preparation for the prevention and/or treatment of skin ulcers that contains Muse cells.

Means for Solving the Problems

The inventors of the present invention found that, by administering Muse cells to mice with diabetic skin ulcer, the Muse cells are able to reconstruct and repair skin tissue that results in healing of the ulcer, thereby leading to completion of the present invention.

Namely, the present invention is as described below.

[1] A cell preparation for preventing and/or treating skin ulcer, comprising pluripotent stem cells positive for SSEA-3 isolated from biological mesenchymal tissue or cultured mesenchymal cells.

[2] The cell preparation described in [1] above, comprising a cell fraction wherein pluripotent stem cells positive for SSEA-3 have been concentrated by external stress stimulation.

[3] The cell preparation described in [1] or [2] above, wherein the skin ulcer is selected from the group consisting of diabetic skin ulcer, decubitus ulcer, venous stasis ulcer, arterial ulcer, radiation ulcer, necrotizing fasciitis and third degree burns.

[4] The cell preparation described in [1] to [3] above, wherein the pluripotent stem cells are CD105-positive.

[5] The cell preparation described in [1] to [4] above, wherein the pluripotent stem cells are CD117-negative and CD146-negative.

[6] The cell preparation described in [1] to [5] above, wherein the pluripotent stem cells are CD117-negative, CD146-negative, NG2-negative, CD34-negative, vWF-negative and CD271-negative.

[7] The cell preparation described in [1] to [6] above, wherein the pluripotent stem cells are CD34-negative, CD117-negative, CD146-negative, CD271-negative, NG2-negative, vWF-negative, Sox10-negative, Snail-negative, Slug-negative, Tryp1-negative and Dct-negative.

[8] The cell preparation described in [1] to [7] above, wherein the pluripotent stem cells are pluripotent stem cells having all of the following properties:
 (i) low or absent telomerase activity;
 (ii) ability to differentiate into cells of any of the three germ layers;
 (iii) absence of demonstration of neoplastic proliferation; and
 (iv) self-renewal ability.

[9] The cell preparation described in [1] to [8] above, wherein the pluripotent stem cells have the ability to differentiate into one or more cells selected from the group consisting of epidermal keratinocytes, vascular endothelial cells, vascular pericytes, adipocytes, preadipocytes, skin fibroblasts and nerve sheath cells.

Effects of the Invention

The present invention is able to inhibit the progression of skin ulcer and repair skin tissue by a skin tissue regeneration mechanism by which Muse cells differentiate into cells that constitute skin tissue at the site of a skin ulcer following administration of the Muse cells to that site in a subject afflicted with skin ulcer.

BRIEF DESCRIPTION OF THE DRAWINGS

FIG. 1B indicates typical changes in blood sugar levels. Nearly all of the mice became hyperglycemic after one or two injections of STZ.

MODE FOR CARRYING OUT THE INVENTION

Figure 1:
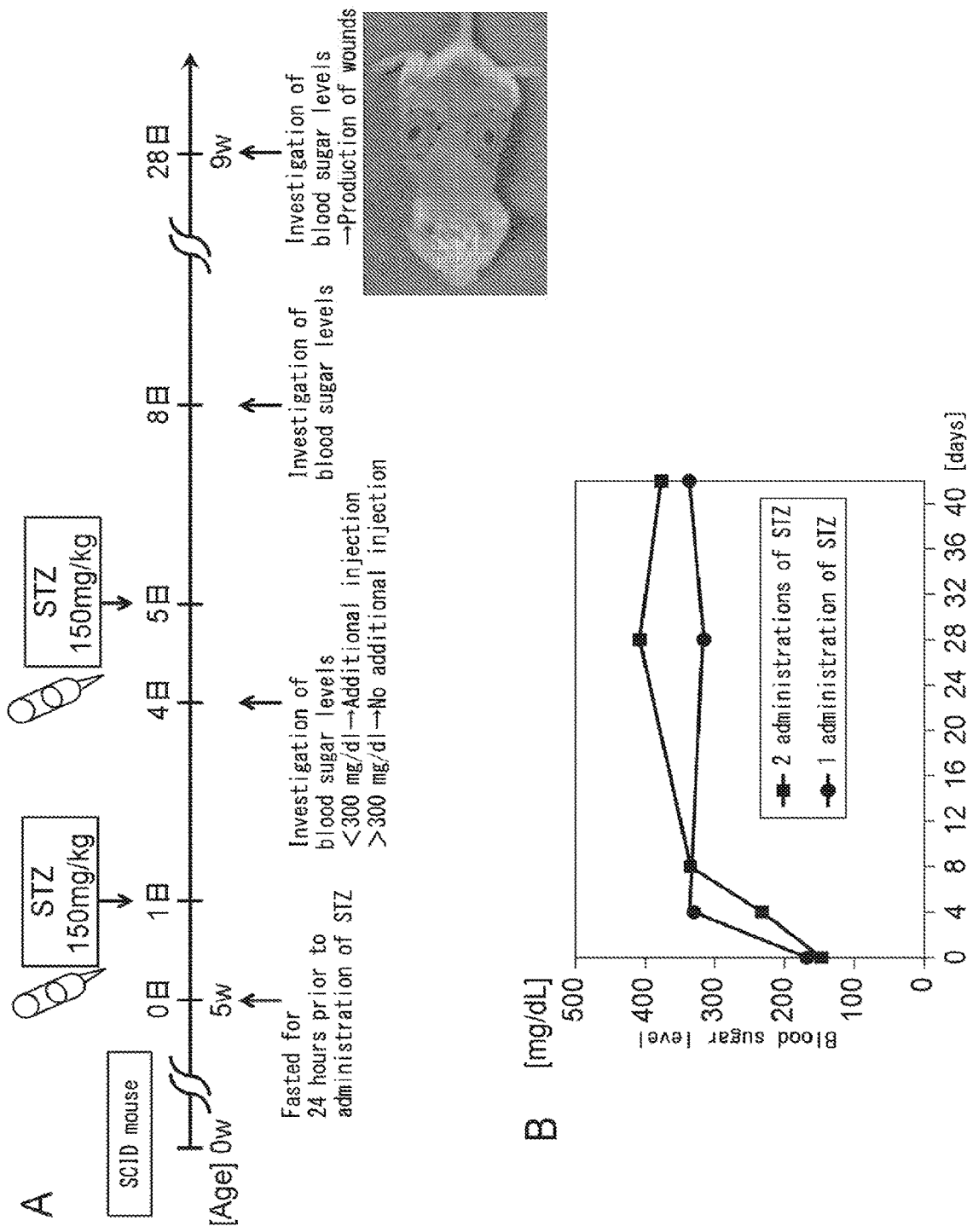
FIG. 1 A. Since mice typically have an inherently high level of wound healing ability that enables wounds to heal rapidly, it is difficult to clearly differentiate differences in wound healing when evaluating the wound healing effect of a drug. Consequently, immunodeficient mice afflicted with diabetes, which is characterized by impaired progression of wound healing, were used to evaluate wound healing effects. In order to induce type 1 diabetes, 5-week-old female SCID mice were intraperitoneally injected with streptozotocin (STZ) after fasting for 24 hours. The mice were investigated for hyperglycemia (blood glucose >300 mg/dl) 3 days after administration of STZ (150 mg/kg). Administration of STZ (150 mg/kg) was repeated in the case hyperglycemia was not observed. Skin defects were produced on the backs of 9-week-old DM-SCID mice.

The present invention relates to a cell preparation for preventing and/or treating skin ulcer that comprises SSEA-3-positive pluripotent stem cells (Muse cells). The following provides a detailed explanation of the present invention.

1. Applicable Diseases

The present invention aims to prevent and/or treat skin ulcer by using a cell preparation comprising SSEA-3-positive pluripotent stem cells (Muse cells). Here, "skin ulcer" refers to damage to the skin normally caused by a defect (exposure of the dermis or subcutaneous tissue) of the tissue surface caused by inflammation. Although there are no limitations on skin ulcers able to be prevented and/or treated by the cell preparation of the present invention, examples thereof include diabetic skin ulcer, decubitus ulcer, venous stasis ulcer, arterial ulcer, radiation ulcer, necrotizing fasciitis and third degree burns. "Diabetic skin ulcer" refers to an extremely refractory skin ulcer caused by damage to vascular endothelial cells attributable to diabetes, and examples thereof include diabetic foot ulcers and diabetic lower leg ulcers. "Decubitus" refers to a chronic ulcer caused by pressure applied over an extended period of time to an area of skin. This type of ulcer is frequently referred to as a bedsore. "Venous stasis ulcer" occurs due to congestion of blood or other fluid from a defective vein. "Arterial ulcer" refers to necrotic skin in an area surrounded by arteries having poor circulation. "Radiation ulcer" indicates an ulcer occurring in irradiated skin. "Necrotizing fasciitis" indicates a soft tissue inflammation that begins with bacterial infection of superficial fascia followed by the rapid spread of necrosis. In addition, "third degree burns" refers to burns extending to the full thickness of the dermal layer and subcutaneous tissue. According to the present invention, the cell preparation of the present invention is effective for preventing and/or treating diabetic skin ulcer in particular.

2. Cell Preparation (1) Pluripotent Stem Cells (Muse Cells)

The existence of the pluripotent stem cells used in the cell preparation of the present invention was discovered by Dezawa, one of the inventors of the present invention, and the cells were named multilineage-differentiating stress enduring (Muse) cells. Muse cells can be obtained from bone marrow, adipocytes (Ogura, F., et al., Stem Cells Dev., Vol. 23, p. 717-728 (2014)) and skin tissue such as dermal connective tissue, and are also sporadically present in the connective tissue of various organs. In addition, these cells have the properties of both pluripotent stem cells and mesenchymal stem cells, and are identified as being double positive for each of the cell surface markers of stage-specific embryonic antigen-3 (SSEA-3) and CD105. Thus, Muse cells or cell populations containing Muse cells can be isolated from body tissue by using these antigen markers as indicators. In addition, cell populations containing Muse cells can be concentrated by long-term exposure to stress caused by hypoxia or proteases such as trypsin or dispase. Details regarding the isolation, identification and characteristics of Muse cells are disclosed in International Publication No. WO 2011/007900. In addition, as was reported by Wakao, et al. (2011, previously described), in the case of culturing mesenchymal cells from bone marrow or skin and the like and using those cells as a Muse cell parent population, all SSEA-3-positive cells were determined to be CD105-positive cells. Thus, in the cell preparation of the present invention, in the case of isolating Muse cells from the mesenchymal tissue of a body or cultured mesenchymal cells, Muse cells can be purified and used by simply using SSEA-3 as an antigen marker. Furthermore, in the present description, pluripotent stem cells (Muse cells) or a cell population containing Muse cells that has been isolated from the mesenchymal tissue of a body or cultured mesenchymal cells by using SSEA-3 as an antigen marker may simply be described as "SSEA-3-positive cells".

Simply put, Muse cells or cell populations containing Muse cells can be isolated from body tissue (such as mesenchymal tissue) by using only antibody to a cell surface marker in the form of SSEA-3 or by using antibodies to both SSEA-3 and CD105. Here, a "body" refers to the body of a mammal. In the present invention, a body does not include fertilized eggs or embryos in an earlier stage of development than the blastocyst stage, but includes fetuses and embryos in a stage of development beyond the blastocyst stage including blastula. Examples of mammals include, but are not limited to, primates such as humans or monkeys, rodents such as mice, rats, rabbits or guinea pigs, as well as cats, dogs, sheep, pigs, cows, horses, donkeys, goats and ferrets. The Muse cells used in the cell preparation of the present invention are clearly distinguished from embryonic stem (ES) cells and iPS cells in that they are isolated directly from the body by means of a marker. In addition, "mesenchymal tissue" refers to tissue present in tissue or various organs such as bone, periosteum, blood, bone marrow, skeletal muscle, dermis, ligaments, tendons, dental pulp, umbilical cord or umbilical cord blood. For example, Muse cells can be obtained from bone marrow, skin and adipose tissue. Muse cells are preferably used, for example, by collecting mesenchymal tissue from a body and isolating Muse cells from this tissue. In addition, Muse cells may also be isolated from cultured mesenchymal cells such as fibroblasts or bone marrow mesenchymal stem cells using the aforementioned isolation means. Furthermore, Muse cells used in the cell preparation of the present invention may be autologous or heterologous with respect to the recipient of a cell transplant.

As was previously described, although Muse cells or cell populations containing Muse cells can be isolated from body tissue by being positive for SSEA-3 indicator or being double positive for SSEA-3 and CD105 indicators, various types of stem cells and precursor cells are known to be contained in human adult skin. However, Muse cells are not the same as these cells. Examples of these stem cells and precursor cells include skin-derived precursor cells (SKP), nerve cell stem cells (NCSC), melanoblasts (MB), perivascular cells (PC), endothelial precursor cells (EP) and adipose-derived stem cells (ADSC). Muse cells can be isolated by using "non-expression" of markers unique to these cells as an indicator. More specifically, Muse cells can be isolated by using as an indicator the non-expression of at least 1, and for example, 2, 3, 4, 5, 6, 7, 8, 9, 10 or 11 markers selected from the group consisting of CD34 (marker for EP and ADSC), CD117 (c-kit) (marker for MB), CD146 (marker for PC and ADSC), CD271 (NGFR) (marker for NCSC), NG2 (marker for PC), vWF factor (von Willebrand factor) (marker for EP), Sox10 (marker for NCSC), Snail (marker for SKP), Slug (marker for SKP), Tyrp1 (marker for MB) and Dct (marker for MB). For example, although not limited thereto, Muse cells can be isolated by using non-expression of CD117 and CD146, non-expression of CD117, CD146, NG2, CD34 vWF and CD271, or using non-expression of the aforementioned 11 markers as an indicator.

In addition, Muse cells having the aforementioned characteristics used in the cell preparation of the present invention may have at least one property selected from the group consisting of:

(i) low or absent telomerase activity;

(ii) ability to differentiate into cells of any of the three germ layers;

(iii) absence of demonstration of neoplastic proliferation; and (iv) self-renewal.

In one aspect of the present invention, Muse cells used in the cell preparation of the present invention have all of the aforementioned properties. Here, the "low or absent telomerase activity" of i) refers to having low telomerase activity or being unable to detect telomerase activity in the case of attempting to detect telomerase activity using, for example, the Trapeze XL Telomerase Detection Kit (Millipore). Low telomerase activity refers to having telomerase activity roughly equal to that of somatic cells in the form of human fibroblasts or having telomerase activity equal to $\frac{1}{5}$ or less and preferably $\frac{1}{10}$ or less that of Hela cells. The Muse cells referred to in ii) have the ability to differentiate into the three germ layers (endoderm, mesoderm and ectoderm) in vitro and in vivo, and are able to differentiate into, for example, liver cells, nerve cells, skeletal muscle cells, smooth muscle cells, osteocytes or adipocytes by subjecting to culturing to induce differentiation in vitro. In addition, they may also demonstrate the ability to differentiate into the three germ layers in vivo in the case of transplanting to the testes. Moreover, they also have the ability to migrate to and become established in damaged organs (such as the heart, skin, spinal cord, liver or muscle) and subsequently differentiate into cells corresponding to that tissue by being transplanted into the body by intravenous injection. Although the Muse cells referred to in iii) have the property of proliferating at a growth rate of about 1.3 days during suspension culturing, and discontinuing to grow after about 14 days after growing from a single cell and forming an embryoid body-like cell mass during suspension culturing, when these embryoid body-like cell masses are subjected to adherent culturing, cell growth resumes and cells that have grown from the cell masses begin to disseminate. Moreover, these Muse cells also have the property of not undergoing malignant transformation for at least six months in the case of having transplanted into the testes. In addition, the Muse cells referred to in iv) have the ability to undergo self-renewal. Here, "self-renewal" refers to being able to confirm differentiation into tridermic cells from cells contained in am embryoid body-like cell mass obtained by culturing in a suspension culture starting from a single Muse cell, while at the same time being able to again confirm tridermic differentiation and embryoid body-like cell masses during suspension culturing following the formation of next-generation embryoid body-like cell masses by again subjecting cells of the embryoid body-like cell mass to suspension culturing. Self-renewal may be repeated for a single cycle or a plurality of cycles.

(2) Preparation and Use of Cell Preparation

Although not limited thereto, the cell preparation of the present invention is obtained by suspending the Muse cells or cell population containing Muse cells obtained in the aforementioned section (1) in physiological saline or a suitable buffer (such as phosphate-buffered physiological saline). In this case, if the number of Muse cells isolated from autologous or heterologous tissue is low, the cells may be cultured prior to transplant to increase the number of cells until the prescribed cell density is obtained. Furthermore, since Muse cells do not undergo neoplastic transformation as was previously reported (International Publication No. WO 2011/007900), the possibility of undergoing malignant transformation is low, thereby making these cells safe even if cells recovered from body tissue are contained while still in an undifferentiated state. In addition, although there are no particular limitations thereon, the recovered Muse cells can be cultured in ordinary growth medium (such as α-minimum essential medium (α-MEM) containing 10% calf serum). More specifically, during culturing and proliferation of Muse cells with reference to the aforementioned International Publication No. WO 2011/007900, a solution containing a prescribed Muse cell density can be prepared by suitably selecting the medium and additives (such as antibiotic or serum). In the case of administering the cell preparation of the present invention to a human subject, roughly several milliliters of bone marrow fluid are collected from human ilium, and after allowing the cells to proliferate until a number of cells is reached that enables isolation of an effective therapeutic amount of Muse cells by, for example, culturing bone marrow mesenchymal cells from the bone marrow fluid in the form of adherent cells, the Muse cells can be isolated using an antigen marker in the form of SSEA-3 as an indicator to prepare a solution containing Muse cells at a prescribed density. Alternatively, Muse cells can be prepared in the form of a cell preparation by concentrating a cell population containing Muse cells by exposing to stress caused by hypoxia or protease. Alternatively, autologous Muse cells can be prepared in the form of a cell preparation by isolating Muse cells using SSEA-3 antigen marker as an indicator followed by increasing the number of cells by culturing until a prescribed therapeutic amount is reached.

In addition, in the case of using Muse cells in a cell preparation, dimethylsulfoxide (DMSO) or serum albumin and the like may be contained in the cell preparation to protect the cells and antibiotic may be contained to prevent contamination and growth of bacteria. Moreover, other pharmaceutically acceptable components (such as a carrier, excipient, disintegrating agent, buffer, emulsifier, suspending agent, soothing agent, stabilizer, preservative, antiseptic or physiological saline) or cells or components other than Muse cells contained in mesenchymal stem cells may also be contained in the cell preparation. A person with ordinary skill in the art is able to add these factors and drugs to the cell preparation at suitable concentrations thereof. In this manner, Muse cells can be used as a pharmaceutical composition containing various types of additives.

The number of Muse cells contained in the cell preparation prepared as described above can be suitably adjusted in consideration of such factors as the gender, age and body weight of the subject, status of the affected area or status of the cells used so as to obtain a desired effect when treating skin ulcer (such as reconstruction of skin tissue). In Examples 3 to 5 to be subsequently described, various effects of transplanting Muse cells were examined in an immunodeficient diabetic mouse model produced by administering streptozotocin (STZ). Extremely superior effects were obtained by administering SSEA-3-positive cells to SCID mice weighing approximately 20 g to 30 g at $1.0\times10^5$ cells/animal. On the basis of this result, superior effects can be expected to be obtained by administering an amount of cells equivalent to $3.3\times10^6$ to $5\times10^6$ cells/kg per individual mammal. Furthermore, examples of individuals include, but are not limited to, mice and humans. In addition, the cell preparation of the present invention may be administered a plurality of times (such as 2 to 10 times) at a suitable interval (such as twice a day, once a day, twice a week, once a week, once every two weeks, once a month, once every two months, once every three months or once every six months) until the desired therapeutic effect is obtained. Thus, although varying according to the status of the subject, the therapeutically effective amount is preferably, for example, a dosage of $1\times10^3$ cells to $1\times10^7$ cells per individual administered 1 to 10 times. Examples of the total administered dosage per individual include, but are not limited to, $1\times10^3$ cells to $1\times10^8$ cells, $1\times10^4$ cells to $5\times10^7$ cells, $2\times10^4$ cells to $2\times10^7$ cells, $5\times10^4$ cells to $5\times10^6$ cells and $1\times10^5$ cells to $1\times10^6$ cells.

3. Production of Mouse Diabetic Skin Ulcer Model and Therapeutic Effect of Muse Cells In the present description, a mouse diabetic skin ulcer model can be produced and used to examine the therapeutic effects of the cell preparation of the present invention on skin ulcer. Although there are no particular limitations thereon, examples of mice used in this model typically include SCID mice and Balb/c mice. The diabetic skin ulcer model can be produced by intraperitoneal administration of streptozotocin (STZ) to these mice. STZ is a glucose derivative that damages p cells of the pancreas, and is used to cause the onset of diabetes in animals. According to the present invention, the dosage of STZ is preferably 150 mg/kg per administration and may be administered multiple times.

Since the cell preparation of the present invention comprises human-derived Muse cells, the cells are heterogeneous with respect to the mice administered the preparation. Normally, in experiments in model mice in which cells from a different species are administered thereto, an immunosuppressant (such as cyclosporine) is administered prior or simultaneous to administration of the heterologous cells in order to suppress rejection of the heterologous cells in the body. The inventors of the present invention previously found that a Muse cell parent population in the form of mesenchymal cells inherently demonstrates potent immunosuppression and that Muse cells also demonstrate a similar action. Thus, in the present invention, the use of an immunosuppressant is not required in a mouse model other than SCID mice in which an immunosuppressant is not used.

In an embodiment of the present invention, the cell preparation of the present invention is able to reconstruct normal tissue by treating skin ulcer of a patient. Here, "reconstructing normal tissue" refers to an affected area having a skin ulcer being completely treated as a result of healing the wound. The state of the reconstructed skin is preferably such that the surface thereof is completely covered with epidermal keratinocytes and epithelization has been completed. Moreover, dermis of an adequate thickness is more preferably constructed beneath the epidermis. Even more preferably, skin appendages such as sweat glands and/or hair follicles are additionally regenerated.

According to another mode of the present invention, various cytokines can be made to be secreted from the Muse cells by culturing the Muse cells in a hypoxic state (such as at an oxygen concentration of 1%) (see Example 3). Thus, according to the present invention, a method is provided for increasing production capacity of at least one cytokine among VEGF, EGF, PDGF-BB, NGF-β, SCF, TNF-α, bFGF and TGF-β.

Although the following provides a more detailed explanation of the present invention using the following examples, the present invention is not limited in any way by these examples.

EXAMPLES

Example 1: Preparation of Human Muse Cells (1) Sampling of Human Tissue and Cell Preparation Lipoaspirates were acquired by liposuction surgery from the abdomens and/or thighs of five non-obese women (age: 26.6±8.7 years, BMI: 21.5±2.0) from whom consent was obtained with the approval of the ethics committee of the Graduate School of Medicine and Faculty of Medicine of the University of Tokyo. Stromal vascular fractions (SVF) containing adipose-derived stromal/stem cells (ASC) were isolated from the aspirated adipose tissue as previously described (see Yoshimura, K. et al., J. Cell Physiol., Vol. 208, p. 64-76 (2006)). Simply put, aspirated adipose tissue was washed with PBS and digested in PBS containing 0.075% collagenase for 30 minutes at 37° C. on a shaker. Mature adipocytes and connective tissue were separated from the pellet by centrifugal separation. The cell pellet was then re-suspended and lysed by passing through 100 μm, 70 μm and 40 μm screens. The cell pellet containing adipose-derived stromal/stem cells (ASC) (equivalent to SVF) was cultured in a culture dish containing Dulbecco's Modified Eagle's Medium (DMEM, Nissui, Tokyo, Japan) enriched with 10% fetal bovine serum (FBS). The ASC that proliferated about 2 weeks after culturing were sub-cultured using the same medium. The second generation of sub-cultured hASC were recovered over the course of 5 minutes at 37° C. using 0.25% trypsin containing 2 mM EDTA and then used to isolate Muse cells.

(2) Isolation of Muse Cells

A magnetic-activated cell sorter (MACS, autoMACS, Miltenyl Biotec, Bergisch Gladbach, Germany) was used to recover SSEA-3-positive Muse cells. Since Muse cells expressed SSEA-3 on the surface thereof, anti-SSEA-3 antibody coupled to phycoerythrin (PE, 1:3 dilution, Miltenyl Biotec) and anti-PE microbeads (1:2 dilution, Miltenyl Biotec) were used for MACS isolation of the Muse cells. Target cells labeled with microbeads were trapped in the magnetic field followed by recovery in the form of a positive fraction. The cell solution that did not bind to the magnetic column was recovered in the form of a negative fraction. A MACS program was used in which the cell solution was applied twice to the magnetic column at an extremely slow speed in order to more favorably purify the Muse cells. The resulting positive cell fraction was used in the following examples as a Muse cell population, while the negative cell fraction was used as mesenchymal cell fraction (MSC).

Example 2: Production of Immunosuppressed Diabetic Mice Model

Five-week-old severe combined immunodeficient (SCID) mice (C. B17/Icr-scid scid/scid) were purchased from Clea Japan, Inc. (Tokyo, Japan). All animal experiments were carried out with the approval of the Institutional Animal Care and Use Committee of the University of Tokyo. After allowing the SCID mice to fast for 24 hours, the animals were intraperitoneally injected with freshly prepared citrate-buffered saline (pH 4.5) containing streptozotocin (STZ, 150 mg/kg, Sigma-Aldrich, St. Louis Mo.). Blood glucose levels were measured using a glucometer and test strips (Glucose Pilot, Aventir Biotech LLC, Carlsbad, Calif.) on the third day after injection of STZ. Mice were considered to have diabetes mellitus (DM) if blood glucose level exceeded 300 mg/dl. Those mice that did not exhibit hyperglycemia (blood glucose level in excess of 300 mg/dl) were subjected to a second round of STZ injection (150 mg/kg) followed by monitoring blood glucose levels three days later.

Skin defects were produced on the backs of the mice as previously described (see Galiano, R. D., et al., Wound Repair Regen., Vol. 12, p. 485-492 (2004) and Tepper, O. M., Diabetes, Vol. 10, 2337/db09-0185) in order to evaluate healing of skin wounds. More specifically, each mouse was anesthetized by intraperitoneal injection of pentobarbital (65 mg/kg). After shaving the backs of the animals with an electric trimmer and depilatory cream, two full-thickness skin wounds (diameter: 6 mm) penetrating to the dermomuscular layer were produced on the backs of the mice using a sterilized circular biopsy punch (Kai Industries Co., Tokyo, Japan). A doughnut-shaped silicon splint (silicon rubber sheet having an inner diameter of 9 mm, outer diameter of 15 mm and thickness of 1.0 mm, Kyowa Industries, Saitama, Japan) was placed on the wounds and fixed in position using 6-0 nylon suture to avoid contraction of the wound (FIG. 1A). An occlusive bandage (Perme-roll, Nitto Medical, Osaka, Japan) was used to prevent the wound from drying and forming a scab.

Five experimental groups were prepared consisting of wild-type mice, non-DM-SCID mice, DM-induced SCID mice, DM-induced SCID mice treated with the Muse cell population, and DM-induced SCID mice treated with the mesenchymal cell fraction (MSC). Six mice were used in each group. Muse cells ($1.0 \times 10^5$ cells/mouse) were mixed with 0.1 ml of crosslinked hyaluronic acid (Restylane, Q-MED, Uppsala, Sweden) followed by injecting subcutaneously around the wounds. The amount of time until wound closure (number of days until complete epidermal regeneration) was investigated macroscopically. The wounds were sequentially photographed on days 0, 3, 7, 10 and 14 using an ordinary digital camera (IXY Digital 90, Canon, Tokyo, Japan). The photographs were evaluated using image analysis software (Photoshop CS6, Adobe Systems, San Jose, Calif.) followed by measurement of wound area.

Example 3: Cytokine Production Assay (ELISA)

MSC are known to secrete growth factors (such as PDGF, bFGF, TGF-β or EGF) required in the inflammatory phase and cell growth phase of wound healing (Maxson, S., et al., Stem Cells Transl. Med., Vol. 1, p. 142-149 (2012)). Therefore, the Muse cell population and MSC were cultured in vitro under hypoxic and normoxic conditions to examine cytokines secreted into the culture broth. The experiment was carried out in the manner indicated below. $4.0 \times 10^5$ cells of the Muse cell population and MSC were disseminated in a 60 mm culture dish followed by culturing in serum-free DMEM under hypoxic (1% $O_2$) and normoxic (6% $O_2$) conditions. The culture medium was recovered 48 hours later and filtered using a 0.22 μm filter (Millex-GV Filter, Millipore, Billerica, Mass.). The amounts of cytokines secreted into the culture broth were compared and examined using an ELISA kit for hepatocyte growth factor (HGF) and stromal cell-derived factor 1 (SDF-1) (both available from R&D Systems, Minneapolis, Minn.), and using a cytokine array kit for vascular endothelial growth factor (VEGF), epidermal growth factor (EGF), platelet-derived growth factor (PDGF-BB), nerve growth factor-β (NGF-β), steam cell factor (SCF), tumor necrosis factor-α (TNF-α), basic fibroblast growth factor (bFGF) and transforming growth factor-β (TGF-β) (Signosis #EA-1101, Santa Clara, Calif.). Absorbance was measured at 450 nm by spectrophotometry using an Infinite microplate reader (M1000, Tecan Group, Mannedorf, Switzerland).

Figure 2:
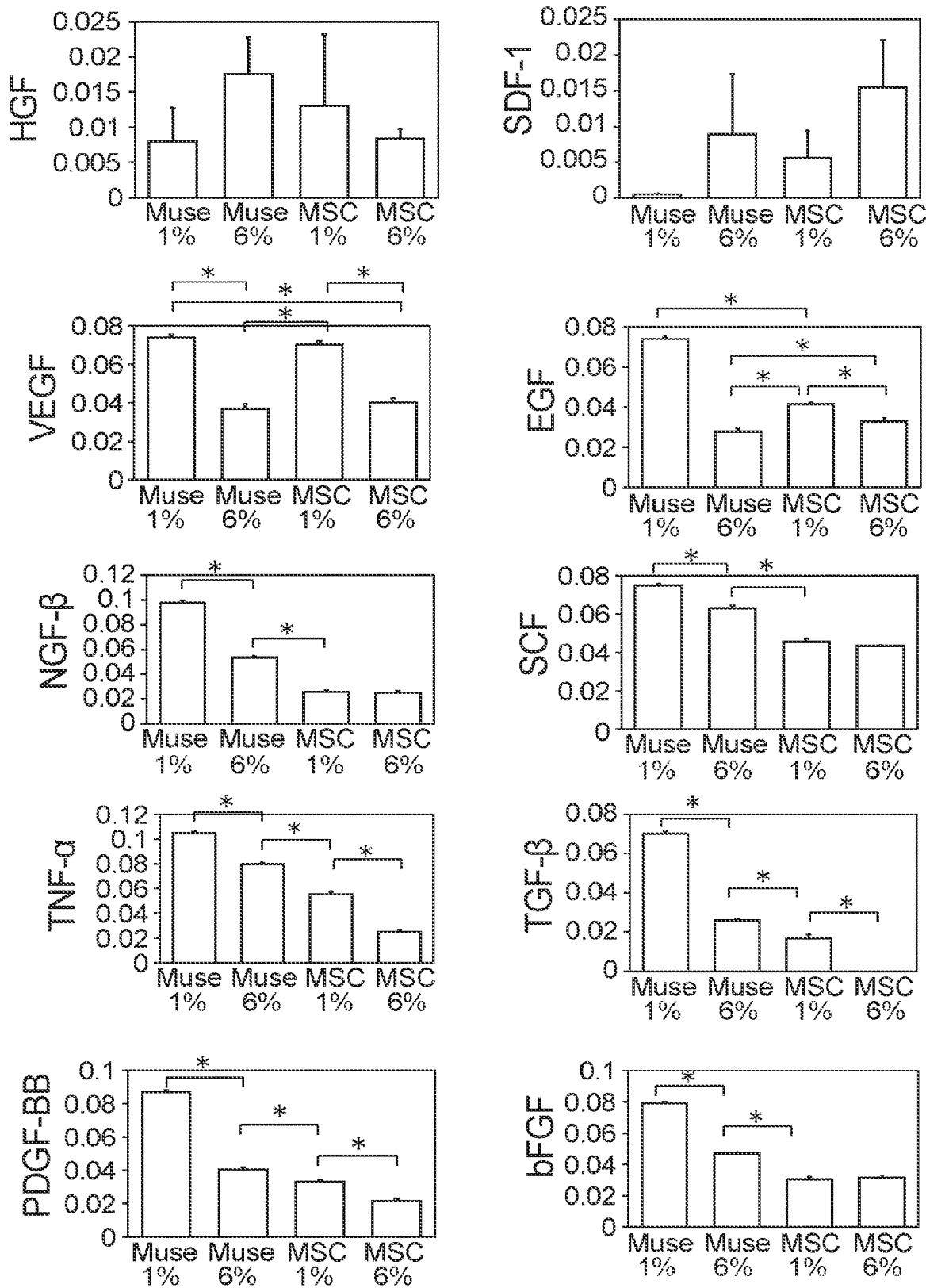
FIG. 2 MSC are known secrete a growth factor required during the inflammatory phase and cell growth phase of wound healing. Therefore, the relative values of growth factor production in Muse cell fractions and mesenchymal cell fractions (MSC) cultured for 48 hours under hypoxic (1% $O_2$) and normoxic conditions were measured by ELISA. The measured cytokines consisted of HGF, SDF-1, PDGF-BB, VEGF, EGF, TGF-$\beta$, NGF-$\beta$, bFGF and TNF-$\alpha$. Absorbance at 450 nm is plotted on the Y axis. Values are shown as the mean±SD (n=3). Asterisks (*) indicate P<0.05.

The results of adherent culturing of the Muse cell population and MSC under normoxic (6% $O_2$) and hypoxic (1% $O_2$) conditions and comparing the concentrations of cytokines present in the culture medium 48 hours later are shown in FIG. 2. The Larger amounts of EGF, PDGF-BB, NGF-β, SCF, TNF-α, bFGF and TGF-β were detected in the Muse cell population in comparison with MSC cultured at the same oxygen pressure. Moreover, the concentrations of VEGF, EGF, PDGF-BB, NGF-β, SCF, TNF-α, bFGF and TGF-β were higher in the Muse cell population under hypoxic conditions than the concentrations thereof under normoxic conditions.

Example 4: Wound Healing in DM-SCID Mice

Although streptozotocin (STZ) induced type 1 DM by damaging pancreas β cells, the administration dosage and method of STZ differed from those of previous reports (see Schmidt, R. E., et al., Am. J. Pathol., Vol. 163, p. 2077-2091 (2003); Lee, R. H., et al., Proc. Natl. Acad. Sci. USA, Vol. 103, p. 17438-17443 (2006); and, Schmidt, R. E., et al., Exp. Neurol., Vol. 209, p. 161-170 (2008)). When STZ was administered at 200 mg/kg, many of the SCID mice died within 1 week after administration due to severe weight loss and metabolic abnormalities. However, when STZ was injected into SCID mice 24 hours after the start of fasting at 150 mg/kg, hyperglycemia was able to be induced comparatively consistently and a state of DM (blood glucose level exceeding 300 mg/dl) continued for more than 30 days (FIG. 1B). Those SCID mice in which DM was successfully induced by injection of STZ in a single administration (9 of 29 mice: 31.0%) or after two administrations (13 of 29 mice: 44.8%) were used in a wound healing experiment for 30 days after the final injection of STZ.

Figure 3:
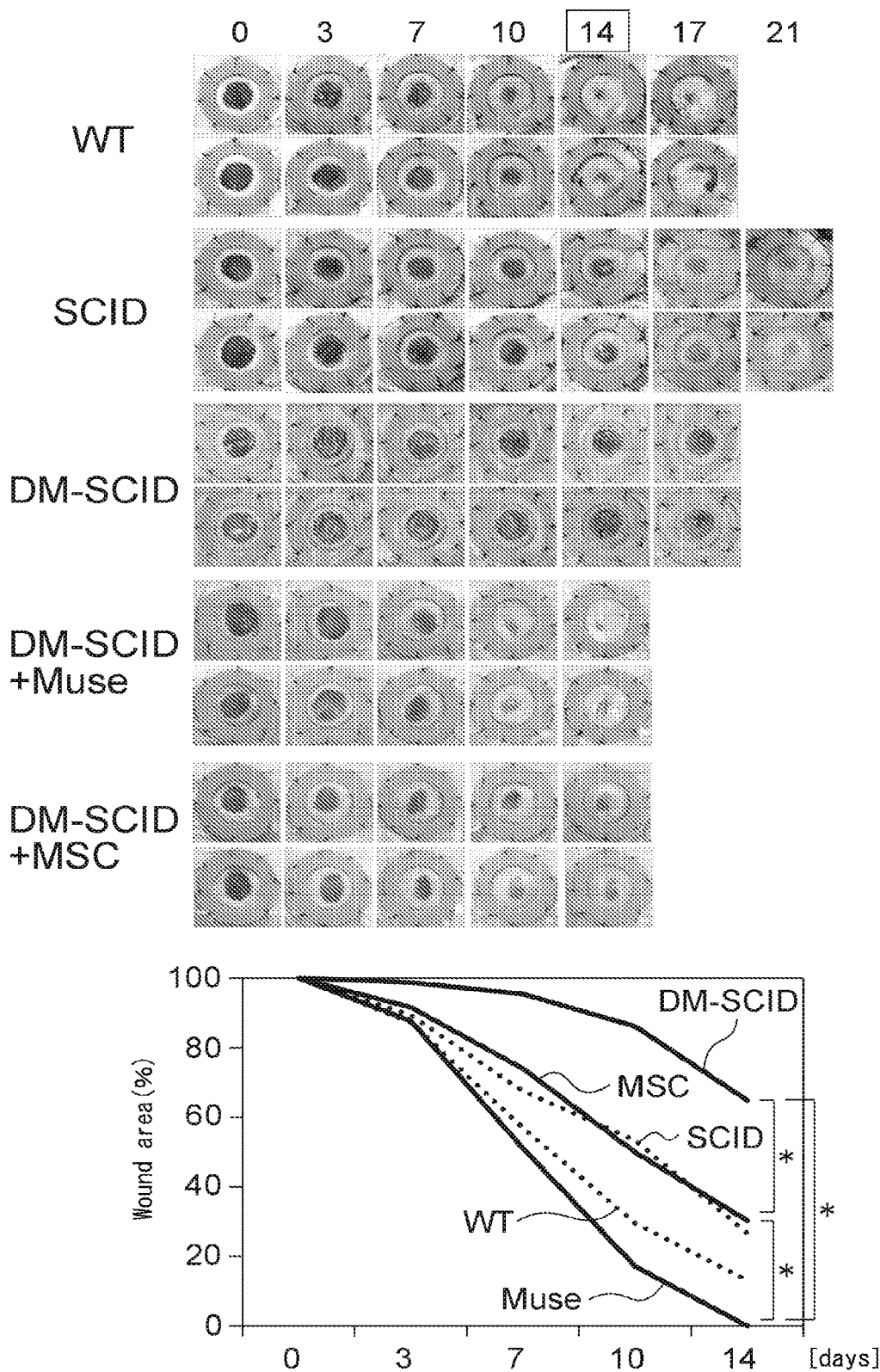
FIG. 3 Wound healing of skin defects (diameter: 6 mm) were sequentially evaluated through day 14. The wounds were photographed and the ratio (%) of the wound area to the original size of the wound was calculated using digital image analysis software. Although wound healing was observed to be somewhat slower in the SCID mice in comparison with wild-type mice (WT), wound healing in the STZ-induced DM-SCID mice was impaired to a greater extent than in the SCID mice. Wound closure was significantly faster in the DM-SCID mice treated with the Muse cell population than untreated DM-SCID mice, and these mice demonstrated favorable wound healing in comparison with the DM-SCID mice treated with MSC (*P<0.05).

Wound healing was significantly delayed in DM-SCID mice in the case of comparing with wild-type (WT) mice (n=6) or non-DM-SCID mice (n=6) (FIG. 3). Although WT mice and non-DM-SCID mice demonstrated wound sizes of 56.9±12.0% and 67.5±6.5%, respectively, on day 7, DM-SCID mice (n=6) demonstrated wound sizes of 95.4±3.1% (WT vs. DM-SCID: P<0.0001). In addition, DM-SCID mice also demonstrated larger wound sizes than the WT mice or non-DM-SCID mice on day 14. Thus, the DM-SCID mice were confirmed to be an animal model of immunodeficiency associated with impaired wound healing.

Skin ulcers among the DM-SCID mice were treated by subcutaneously injecting the Muse cell population or MSC. DM-SCID mice treated with Muse cells (n=6) demonstrated wound healing that was superior to DM-SCID mice treated with MSC (n=6). The wound sizes on day 7 of the DM-SCID mice treated with Muse cells and MSC were 51.05±7.2% and 74.0±6.6%, respectively (P<0.0001). On day 14, although wounds of DM-SCID mice treated with Muse cells had healed completely, the wound size of DM-SCID mice treated with MSC was still 30.6±6.7% (P=0.0235). Among the DM-SCID mice treated with Muse cells, wound healing was accelerated and appeared to be comparable to that in the WT group.

Example 5: Histological Analysis

Mouse skin samples were embedded in OCT compound (Sakura Finetek, Tokyo, Japan), frozen in liquid nitrogen and stored at −80° C. until sectioned. The frozen sections (8 μm) were placed on slides and allowed to dry for 20 minutes at room temperature followed by fixing for 1 minute with 4% paraformaldehyde (in PBS) and washing for 5 minutes with PBS. The slides were then stained with hematoxylin and eosin (H&E) and treated for immunohistochemical analysis.

Immunohistochemical analysis was carried out as previously described (see Kuroda, Y., et al., Proc. Natl. Acad. Sci. USA, Vol. 107, p. 8639-8643 (2010)). In order to detect human Golgi protein by means of a horseradish peroxidase (HRP) reaction, the slides were treated for 30 minutes with methanol containing 0.3% hydrogen peroxide to deactivate intrinsic peroxidase activity followed by sequentially incubating with rabbit anti-human 58K Golgi protein (1:100 dilution, Abcam, Cambridge, UK) and donkey anti-rabbit IgG-HRP (1:500 dilution, Jackson ImmunoResearch, West Grove, Pa.). Expression of human 58K Golgi protein was visualized by a peroxidase reaction using 3,3'-diaminobenzidine tetrahydrochloride (DAB). The frozen sections were incubated with the following primary antibodies for observing with a confocal laser scanning microscope: mouse anti-human mitochondria (1:100 dilution, Abcam), rabbit anti-human 58K Golgi protein, rabbit anti-human CK14 (1:200 dilution, Abcam) or goat anti-human platelet endothelial cell adhesion molecule (PECAN-1, dilution: 1:50, Santa Cruz Biotechnology, Santa Cruz, Calif.). Next, the sections were incubated with the following secondary antibodies: donkey anti-mouse IgG-Alexa488, donkey anti-rabbit IgG-Alexa680 or rabbit anti-goat IgG-Alexa488 (all 1:500 dilutions, Invitrogen, Carlsbad, Calif.). Nuclei were counterstained with DAPI and examined using a confocal microscope (C1si Nikon, Nikon, Tokyo, Japan).

Figure 4:
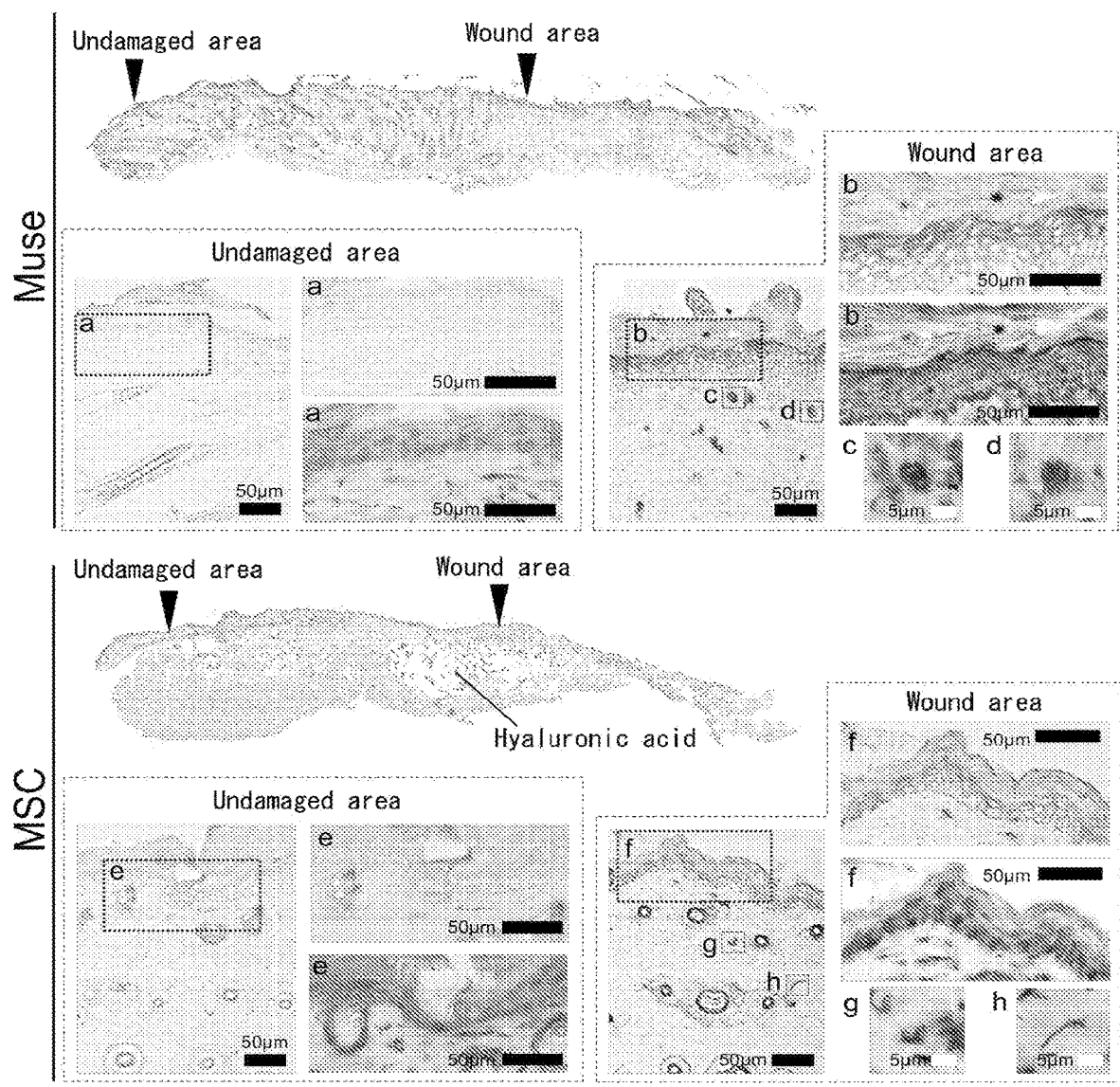
FIG. 4 This indicates the results of an analysis of human Golgi complex in the wounds of DM-SCID mice treated with Muse cells and MSC. Cells positive for human Golgi complex (comparable to transplanted Muse cells) were observed in the epidermis and upper layer of both wound areas treated with Muse cells and MSC after 14 days. However, cells positive for human Golgi complex were not detected in either group in surrounding undamaged areas. Transplanted human cells were detected at a higher frequency in the Muse cell treated samples than in the MSC treated samples.
Figure 5:
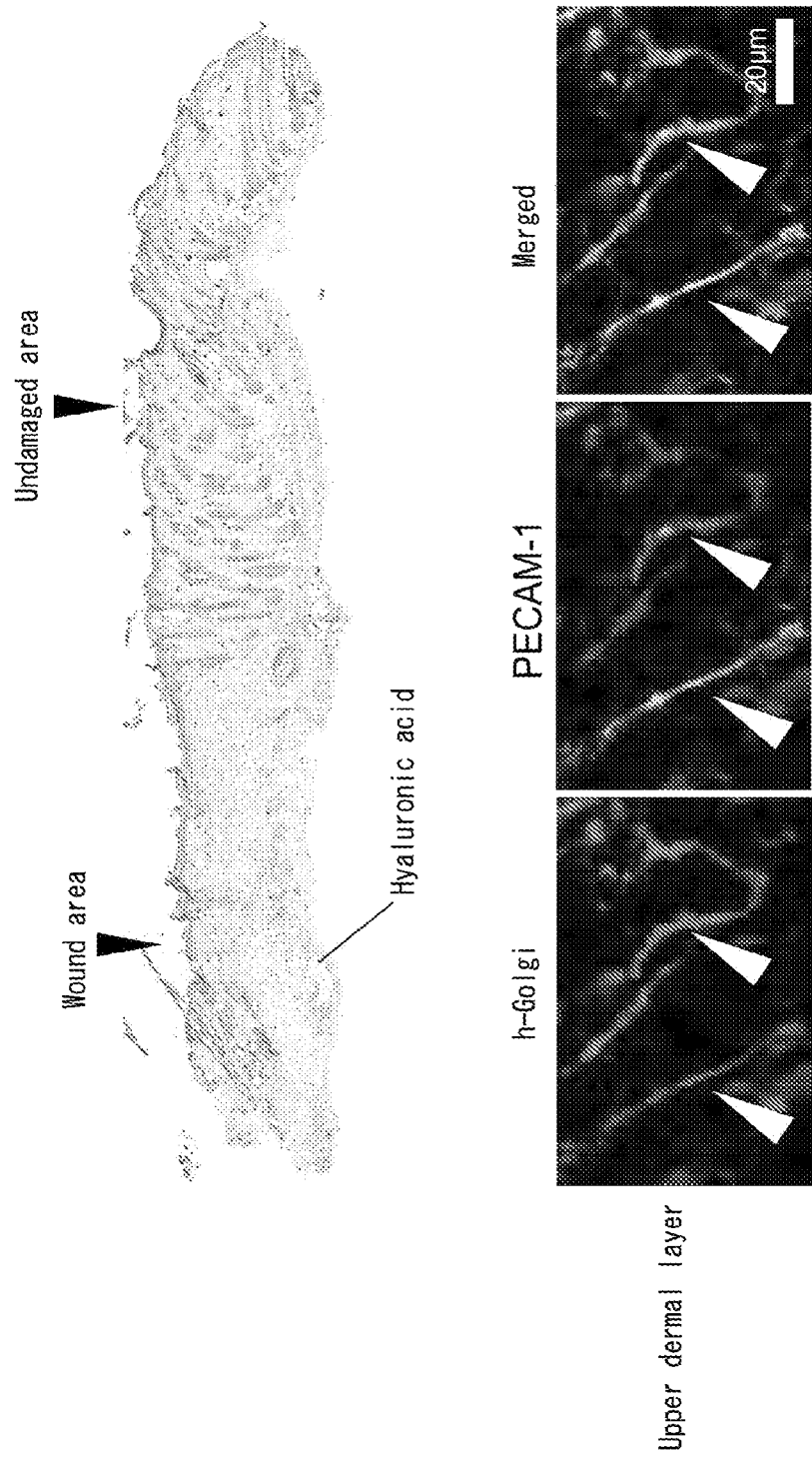
FIG. 5 Human Golgi complex and a differentiation marker (PECAN-1) were subjected to double immunohistochemical staining in order to characterize transplanted Muse cells. Several cells that expressed human Golgi complex were suggested to differentiate into vascular endothelial cells in the dermis since they were positive for PECAM-1.

According to the immunohistochemical analysis of human Golgi complex, transplanted cells were shown to be detected in the epidermis and upper dermal layer in each of the samples treated with the Muse cell population and MSC on day 14. However, cells that expressed human Golgi complex were not observed in surrounding undamaged areas (FIG. 4). In addition, deposition of the injected hyaluronic acid was detected in the subcutaneous layer. Moreover, several cells that expressed human Golgi complex within the dermis were positive for h-PECAM-1 (FIG. 5). This data suggests that transplanted Muse cells are viable in both the epidermis and dermis and are capable of differentiating into epidermal keratinocytes and vascular endothelial cells.

INDUSTRIAL APPLICABILITY

The cell preparation of the present invention is able to reconstruct and repair skin tissue by administering to an area affected by skin ulcer in a mouse model of diabetic skin ulcer, and can therefore be applied to the treatment of diabetic skin ulcer.

All citations and patent publications cited in the present description are incorporated herein in their entirety by reference. Furthermore, although specific embodiments of the present invention have been explained in the present description for the purpose of exemplification, it should be understood by a person with ordinary skill in the art that various modifications can be made thereto without deviating from the spirit and scope of the present invention.

The invention claimed is:

1. A method for preventing and/or treating diabetic skin ulcer in a subject in need thereof, the method comprising administering to said subject a cell preparation comprising pluripotent stem cells positive for SSEA-3 isolated from biological mesenchymal tissue or cultured mesenchymal cells, wherein said pluripotent stem cells are concentrated by subjecting mesenchymal cell population to external stress stimulation or isolated by cell sorting with SSEA-3(+), and wherein the pluripotent stem cells having a plurality of properties comprising:
    (i) CD105-positivity;
    (ii) low or absent telomerase activity;
    (iii) ability to differentiate into embryonic endoderm, ectoderm, and mesoderm germ layers;
    (iv) absence of neoplastic proliferation; and
    (v) ability to self-renew,
    wherein said pluripotent stem cells are administered at a dosage of $1 \times 10^3$ to $1 \times 10^8$ cells per subject.

2. The method according to claim 1, wherein the pluripotent stem cells are CD117-negative and CD146-negative.

3. The method according to claim 1, wherein the pluripotent stem cells are CD117-negative, CD146-negative, NG2-negative, CD34-negative, vWF-negative and CD271-negative.

4. The method according to claim 1, wherein the pluripotent stem cells are CD34-negative, CD117-negative, CD146-negative, CD271-negative, NG2-negative, vWF-negative, Sox10-negative, Snail-negative, Slug-negative, Tryp1-negative and Dct-negative.

5. The method according to claim 1, wherein the pluripotent stem cells have the ability to differentiate into one or more cells selected from the group consisting of epidermal keratinocytes, vascular endothelial cells, vascular pericytes, adipocytes, preadipocytes, skin fibroblasts and nerve sheath cells.

* * * * *